US006825362B2

(12) United States Patent
Dandala et al.

(10) Patent No.: US 6,825,362 B2
(45) Date of Patent: Nov. 30, 2004

(54) PROCESS FOR LACTONIZATION TO PRODUCE HIGHLY PURE SIMVASTATIN

(75) Inventors: Ramesh Dandala, Hyderabad (IN); Sonny Sebastian, Hyderabad (IN); Dandala Subramanyam, Secunderabad (IN); Meenakshisunderam Sivakumaran, Hyderabad (IN)

(73) Assignee: Aurobindo Pharma Limited, Hyderabad (IN)

( * ) Notice: Subject to any disclaimer, the term of this patent is extended or adjusted under 35 U.S.C. 154(b) by 0 days.

(21) Appl. No.: 10/602,463

(22) Filed: Jun. 23, 2003

(65) Prior Publication Data

US 2004/0077884 A1 Apr. 22, 2004

(30) Foreign Application Priority Data

May 16, 2002 (IN) .................. PCT/IN02/00121

(51) Int. Cl.[7] ............................................. C07D 309/10
(52) U.S. Cl. ...................................................... 549/292
(58) Field of Search ......................................... 549/292

(56) References Cited

U.S. PATENT DOCUMENTS 6,573,385 B1 * 6/2003 Sambasivam et al. ...... 546/314
6,649,775 B2 * 11/2003 Lee et al. .................... 549/292

* cited by examiner

Primary Examiner—Taofiq Solola
(74) Attorney, Agent, or Firm—Jay R. Akhave

(57) ABSTRACT

There is disclosed, a process for lactonization to produce highly pure simvastatin of Formula I

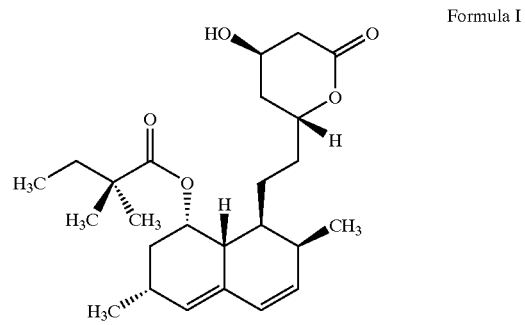

Formula I which comprises lactonization of a compound of Formula II

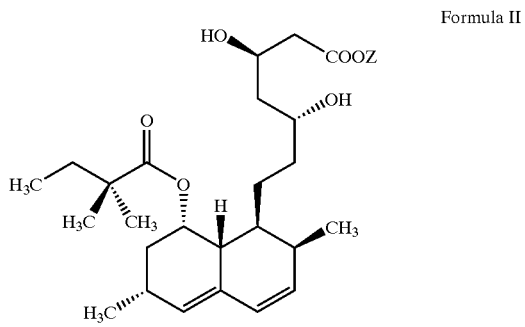

Formula II where Z is H or $NH_4$ in a mixture of acetonitrile and glacial acetic acid under anhydrous conditions at a temperature of 65–70° C.

4 Claims, No Drawings

PROCESS FOR LACTONIZATION TO PRODUCE HIGHLY PURE SIMVASTATIN

| INVENTORS | | |
|---|---|---|
| Name | Residence | Citizenship |
| Ramesh Dandala | 403, Janapriya Pramila Enclave Uma Nagar, Kundangagh, Begumpet Hyderabad - 500 016 (India) | Indian |
| Sonny Sebastian | 505, Vishai Towers, A Block A.S. Raju Nagar, Kukatpally, Hyderabad - 500 072 (India) | Indian |
| Dandala Subramanyam | 12-5A, J.J. Nagar Alwai, Secunderabad - 500 060 (India) | Indian |
| Meenakshisunderam Sivakumaran | D-1, Hidden Treasure Apartments Near Ayyappa Swami Temple Lane Somajiguda, Hyderabad - 500 082 (India) | Indian |

CROSS REFERENCE TO RELATED APPLICATIONS

| Indian Patent Application | Filing Date | May 18, 2001 |
|---|---|---|
| | Application No. | 402/MAS/2001 |
| | Status | Not issued |
| PCT Application | Filing Date | May 16, 2002 |
| | Application No. | PCT/IN02/00121 |
| | Publication Date | Nov. 28, 2002 |
| | Publication No. | WO 02/094803 A1 |

STATEMENT REGARDING FEDERALLY SPONSORED RESEARCH AND DEVELOPMENT

Not Applicable

FIELD OF THE INVENTION

A process for lactonization to produce highly pure simvastatin of Formula I

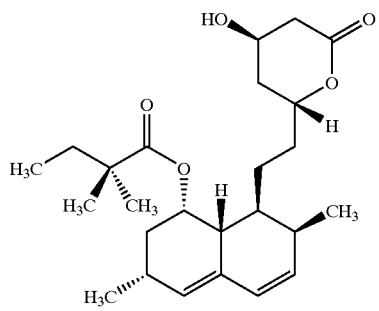

Formula I

BACKGROUND OF THE INVENTION

This invention relates to a process for lactonization to produce highly pure simvastatin.

Lovastatin, simvastatin, pravastatin, atorvastatin and mevastatin are well known potent antihypercholesterolemic agents that function by limiting cholesterol biosynthesis by inhibiting the enzyme, HMG-CoA reductase. This class of compounds, referred to generally as statins, are produced either by natural fermentation process or through semi-synthetic and totally synthetic means thereof. Two of the most popular compounds in this therapeutic category are simvastatin and atorvastatin. The former is one of the most prescribed drugs in the treatment of primary hypercholesterolemia with minimum side effects and well established safety profile. The use of highly pure simvastatin is exceedingly desirable in preparation of a pharmaceutical product as it would avoid accumulation of impurities during prolonged usage and would reduce the possible side effects during medical treatment.

In most of the synthetic methods known to manufacture simvastatin (Formula I) shown below, the compound of Formula IIA also shown below, is the common intermediate, which is cyclized to obtain simvastatin and thus lactonization constitutes an essential step of the synthesis.

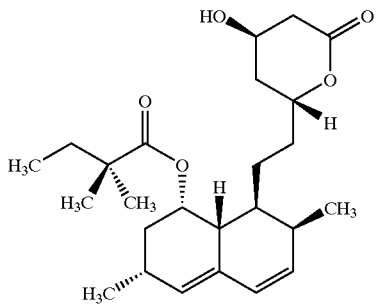

Formula I

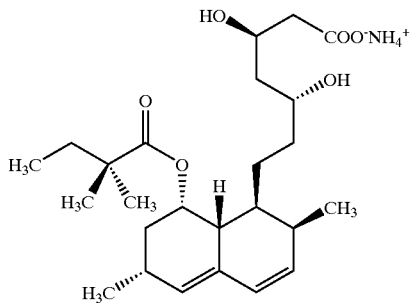

Formula IIA

It is of considerable importance to employ an efficient method for the lactonization that can produce simvastatin of high purity in good yield.

The process disclosed in the U.S. Pat. No. 4,820,850 involves heating of hydroxyacid ammonium salt in toluene at 100° C. under a purge of nitrogen. The lactonization completion requires 6–8 hours refluxing and results in formation of increased amounts of dimer (Formula III).

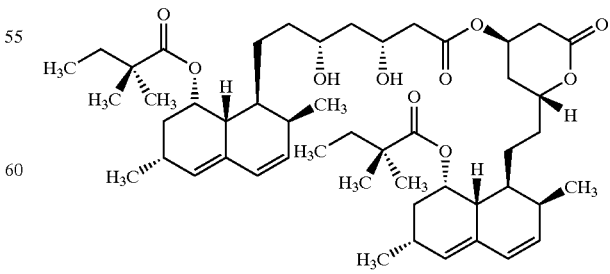

Formula III

This dimer impurity is difficult to separate from the desired lactone even with repeated crystallization. Efforts to minimise the formation of the dimer have led to the use of high dilution during lactonization reaction. Nevertheless, this technique results in lower efficiency and is disadvantageous at commercial scale.

U.S. Pat. No. 4,916,239 describes another process where the lactonization reaction has been carried out by treating hydroxyacid ammonium salt in a mixture of acetic acid and water, and in the presence of a strong acid catalyst. This process requires gradual addition of water in several lots to effect crystallization of the lactonized product from the reaction medium to shift the equilibrium to the lactone side and this drives the lactonization to completion. This process is not amenable to industrial scale due to effluent generation and low purity of simvastatin product even though dimer content obtained is reported to be less than 0.2%.

U.S. Pat. No. 5,917,058 provides an alternate process to lactonize hydroxyacid or its salt by treatment with acetic acid under anhydrous conditions. However, the purity of the final product obtained by this procedure is not more than 99%. Furthermore, in this patent, there is no reference to the level of dimeric impurity produced in the process.

The aim of the present invention is to obtain highly pure simvastatin that contains dimeric impurity less than 0.1%. An example where simvastatin of greater than 99.5% purity has been achieved is cited in WO 99/42601 wherein the product was purified by successive crystallizations from aqueous acetone and from ethyl acetate.

BRIEF STATEMENT OF THE INVENTION

According to this invention, there is provided a process for lactonization to produce highly pure simvastatin of Formula I

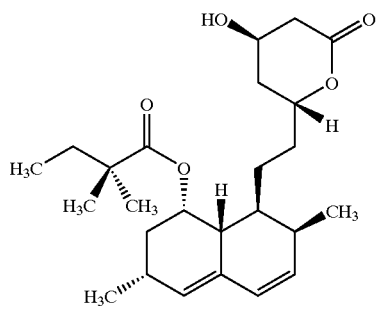

Formula I which comprises lactonization of a compound of the Formula II,

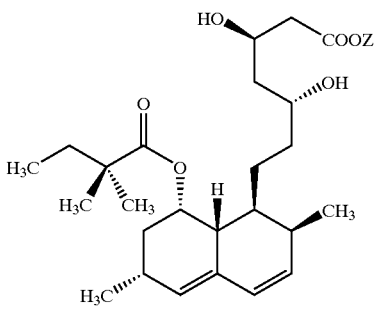

Formula II where Z is H or NH$_4$ in a mixture of acetonitrile and glacial acetic acid under anhydrous conditions at a temperature of 65–70° C. and wherein the dimer impurity of Formula III formed is less than 0.1 and thereafter adding water to the reaction mixture thereby causing simvastatin of Formula I to precipitate from the reaction mixture.

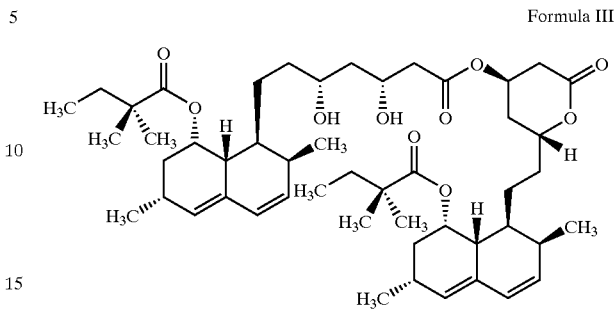

Formula III

In this process in Formula II above, preferably Z is NH$_4$.

The process further comprises adding water to the reaction mixture, thereby causing simvastatin of Formula I to precipitate from the reaction mixture.

DETAILED DESCRIPTION OF THE INVENTION

The instant invention relates to a novel process for lactonization of simvastatin hydroxyacid or its salt that avoids the use of strong corrosive acids and drastic heat conditions. This process allows the lactonization reaction to proceed in a mixture of acetic acid and acetonitrile at moderate temperature and consistently provides simvastatin of greater than 99.5% purity with dimer content less than 0.1%.

Specifically, the process of this invention comprises heating a solution of simvastatin hydroxyacid in its salt form, most preferably the ammonium salt (Formula II) in a mixture of acetic acid and acetonitrile under anhydrous conditions at a temperature that vary from 50° C. to 80° C. and preferably at 65–70° C.

The lactonization reaction is typically accomplished within about 5 to 7 hours. The amount of acetic acid used is at least 3 to 5 parts by volume per part of the starting material. The amount of acetonitrile is 10 to 20 parts by volume per part of the starting material and preferably 15 parts by volume may be used. The lactonized product is isolated after completion of reaction by addition of water.

Major advantage of the present invention as compared to the prior art procedures is the high product purity where the level of dimer impurity has been greatly reduced to less than 0.1%. The addition of water to the reaction mixture directly provides lactone as a homogenous slurry that makes the filtration operation very easy at large scale and work up involves no solvent concentration or neutralisation step prior to product isolation.

The invention will now be more fully described with reference to the following examples which are only illustrative and are not to be construed as any limitation thereof.

EXAMPLE 1

Preparation of (1S,3R,7S,8S,8aR)-3,7-dimethyl-8-[2-[(2R,4R)-4-hydroxy-6-oxo-3,4,5,6-tetrahydro-2H-pyran-2-yl]ethyl]-1,2,3,7,8,8a-hexahydro naphthalin-1-yl 2,2-dimethylbutanoate Lactonization Ammonium 7-[1,2,6,7,8,8a(R)-hexahydro-2(S),6(R)-dimethyl-8(S)-(2,2-dimethylbutyryloxy)-1(S)-naphthyl]-3

(R),5(R)-dihydroxyheptanoate (Formula II) (10 g, 0.022 mol) was dissolved in a mixture of acetonitrile (150 ml) and glacial acetic acid (30 ml). The solution was then heated to 65–70° C. and was maintained at this temperature for 6 hours. At the end of the reaction, HPLC showed simvastatin 97.4%, unreacted starting material 0.69% and dimer 0.07%. The reaction mass was cooled to 15–20° C. and water (350 ml) was added over a period of 30 minutes. The precipitated product was cooled further to 10–15° C. and stirring continued for 1 hour. Product was filtered, washed with water (2×10 ml), 1:2 v/v acetonitrile—water (2×10 ml) and dried in vacuo at 45–50° C. The product thus obtained was dissolved in cyclohexane (200 ml) at 80–85° C. and then cooled over 1 hour to 10–12° C. Product was filtered and washed with chilled cyclohexane (10 ml) and dried in vacuo at 45–50° C. to yield highly pure 8.2 g (89%) of the title compound with HPLC purity 99.63% and dimer impurity 0.04%.

EXAMPLE 2

Preparation of (1S,3R,7S,8S,8aR)-3,7-dimethyl-8-[2-[(2R,4R)-4-hydroxy-6-oxo-3,4,5,6-tetrahydro-2H-pyran-2-yl]ethyl]-1,2,3,7,8,8a-hexahydro naphthalin-1-yl 2,2-dimethylbutanoate Lactonization Ammonium 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II) (10 g, 0.022 mol) was dissolved in a mixture of acetonitrile (150 ml) and glacial acetic acid (30 ml). The reaction mixture was heated at 65–70° C. under anhydrous conditions for 6 hours. Progress of reaction was checked by HPLC. At the end of the reaction, simvastatin was 97.55%, unreacted starting material 0.66% and dimer impurity 0.07%. Thereafter, reaction mixture was cooled to 10–15° C. and water (350 ml) was added slowly over a period of 30 minutes and stirring was continued for 30 minutes. The product was filtered, washed with water (2×10 ml) and dissolved in methanol (90 ml) at 25–30° C. The solution was cooled to 5–10° C. and water (82 ml) was added in 30 minutes. The product thus crystallized was stirred at 5–10° C., filtered and washed with cold methanol/water mixture (1:1 v/v, 8 ml). The product was dried to constant weight in vacuo at 45–50° C. to obtain simvastatin (8.3 g, 90%). Chromatographic purity (HPLC) 99.55% and dimer impurity 0.07%.

We claim:

1. A process for lactonization to produce highly pure simvastatin of Formula I

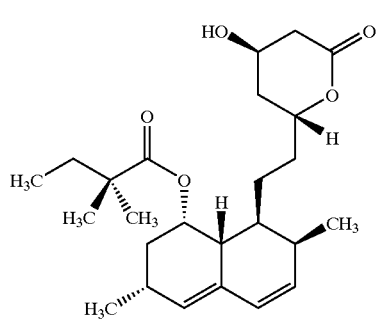

Formula I which comprises the steps of:

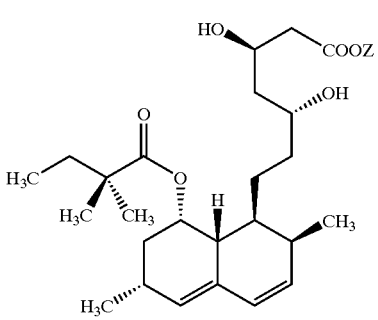

Formula II starting with a compound of Formula II where Z is H or $NH_4$, mixing in a mixture of acetonitrile and glacial acetic acid, reacting the mixture under anhydrous conditions wherein the dimer impurity of Formula III formed is less than 0.1%,

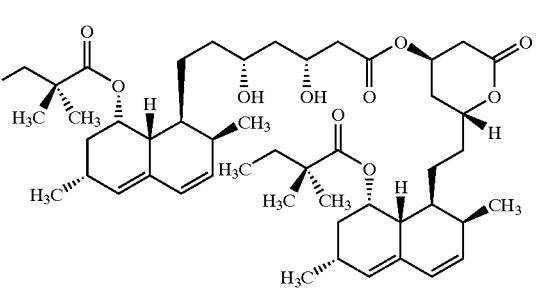

Formula III adding water to the reaction mixture to form a precipitate of simvastatin of Formula I.

2. The process according to claim 1 wherein Z is $NH_4$.

3. The process according to claim 1 wherein the said reaction temperature is 50–80° C.

4. The process according to claim 1 where the said reaction temperature is 60–70° C.

* * * * *